United States Patent
Essig et al.

(10) Patent No.: US 9,957,331 B2
(45) Date of Patent: *May 1, 2018

(54) NON-CROSS-REACTIVE ANTI IGG ANTIBODIES

(75) Inventors: Ulrich Essig, Planegg (DE); Stefan Klostermann, Neuried (DE); Frank Kowalewsky, Munich (DE); Kay-Gunnar Stubenrauch, Penzberg (DE); Rudolf Vogel, Weilheim (DE); Uwe Wessels, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1007 days.

This patent is subject to a terminal disclaimer.

(21) Appl. No.: 13/502,687

(22) PCT Filed: Oct. 18, 2010

(86) PCT No.: PCT/EP2010/065617
§ 371 (c)(1),
(2), (4) Date: Apr. 18, 2012

(87) PCT Pub. No.: WO2011/048043
PCT Pub. Date: Apr. 28, 2011

(65) Prior Publication Data
US 2012/0208216 A1   Aug. 16, 2012

(30) Foreign Application Priority Data

Oct. 19, 2009   (EP) .................................. 09013144

(51) Int. Cl.
*C07K 16/42* (2006.01)
*G01N 33/68* (2006.01)

(52) U.S. Cl.
CPC ..... *C07K 16/4283* (2013.01); *G01N 33/6854* (2013.01)

(58) Field of Classification Search
CPC ............ C07K 16/4283; C07K 2317/33; G01N 33/543; G01N 33/6854; G01N 33/6857; G01N 2800/52
See application file for complete search history.

(56) References Cited

U.S. PATENT DOCUMENTS

| | | | |
|---|---|---|---|
| 5,202,238 A | 4/1993 | Fell et al. | |
| 5,204,244 A | 4/1993 | Fell et al. | |
| 5,332,665 A | 7/1994 | Reed et al. | |
| 5,736,137 A * | 4/1998 | Anderson et al. | 424/133.1 |
| 2005/0169925 A1 | 8/2005 | Bardroff et al. | |
| 2005/0226876 A1 | 10/2005 | Graus et al. | |
| 2008/0118939 A1 * | 5/2008 | Stubenrauch | C07K 16/4208 435/7.94 |

FOREIGN PATENT DOCUMENTS

| | | |
|---|---|---|
| CN | 101088014 | 12/2007 |
| CN | 103068852 | 8/2011 |
| WO | 03/070760 | 8/2003 |
| WO | 2004/087756 | 10/2004 |
| WO | 2004/096274 | 11/2004 |
| WO | 2005/005635 | 1/2005 |
| WO | 2005/023872 | 3/2005 |
| WO | 2005/100402 | 10/2005 |
| WO | 2006/066912 | 6/2006 |
| WO | 2006/072564 | 7/2006 |
| WO | 2008/031532 | 3/2008 |
| WO | 2011/048043 | 4/2011 |
| WO | 2012/022682 | 2/2012 |

OTHER PUBLICATIONS

Abe et al., 1993. Production and immunodiagnostic applications of antihuman light chain monoclonal antibodies. American J. Clinical Pathology 100: 67-74.*
Asada et al., 2002. Molecular evolution of IgG subclass among nonhuman primates: implication of differences in antigenic determinants among apes. Primates 43: 343-349.*
Bourdage et al., 2005. Effect of double antigen bridging immunoassay format on antigen coating concentration dependence and implications for designing immunogenicity assays for monoclonal antibodies. J. Pharmaceut. Biomed. Anal. 39: 685-690.*
Van Schouwenburg et al., 2010. A novel method for the detection of antibodies to adalimumab in the presence of drug reveals "hidden" immunogenicity in rheumatoid arthritis patients. Immunological Meth. 362: 82-88.*
Anonymus, Other Database, (Anti-human IgG . . . URL:http://gelifesciences.com/aptrix/upp00919.nsf/Content/7729A1564E1AB55C1247628001CC069/$file/na933.pdf) Aug. 11, 2010.
Bruck et al., "Purification of mouse monoclonal antibodies from ascitic fluid by DEAE Affi-Gel Blue chromatography" Methods in Enzymology 121:587-596 (1986).
Galfre, G. et al., "Preparation of Monoclonal Antibodies: Strategies and Procedures" Methods in Enzymology 73:3-46 (1981).
Iborra, S. et al., "Vaccination with a plasmid DNA cocktail encoding the nucleosomal histones of Leishmania confers protection against murine cutaneous leishmaniosis" Vaccine 22:3865-3876 ( 2004).
Lonberg, N., "Human antibodies from transgenic animals" Nat Biotechnol 23(9):1117-11125 ( 2005).
Morrison, S. et al., "Chimeric Human Antiody Molecules: Mouse Antigen-binding Domains with Human Constant Region Domains" Proc. Natl. Acad. Sci. USA 81:6851-6855 ( 1984).
Neuberger et al., "A hapten-specific chimaeric IgE antibody with human physiological effector function" Nature 314:268-270 (Mar. 21, 1985).
Riechmann et al. et al., "Reshaping Human Antibodies for Therapy" Nature 332:323-327 (Mar. 24, 1988).

(Continued)

*Primary Examiner* — Ram R Shukla
*Assistant Examiner* — Ellen J Marcsisin
(74) *Attorney, Agent, or Firm* — Grant Kalinowski

(57) ABSTRACT

Herein are reported the cell lines DSM ACC3006, DSM ACC3007, and DSM ACC3008, as well as the antibodies obtained from the cell lines and the use of an antibody obtained from the cell lines in an immunoassay. Also are reported antibodies binding to human or chimpanzee IgG and not binding to canine and marmoset IgG and antibodies specifically binding to an IgG 1 that comprises a kappa light chain constant domain.

12 Claims, 7 Drawing Sheets

(56) References Cited

OTHER PUBLICATIONS

Stubenrauch, K. et al., "Evaluation of an immunoassay for human-specific quantitation of therapeutic antibodies in serum samples from non-human primates" J. of Pharmaceutical and Biomedical Analysis 49:1003-1008 (2009).
Jefferis et al., "Evaluation of monoclonal antibodies having specificity for human IgG subclasses: results of the 2nd IUIS/WHO collaborative study" Immunology Letters, Elsevier 31(2):143-168 (Feb. 1, 1992).
Ware, C.F. et al., "A Rat Anti-Mouse Kappa Chain Specific Monoclonal Antibody, 187.1.10: Purification, Immunochemical Properties and Its Utility as a General Second-Antibody Reagent" 74:93-104 (1984).

* cited by examiner a)

b)

c)

a)

b)

c)

a)

b)

a)

Biotinylated anti-Fc antibody    IgG    Digoxygenylated anti-Fab antibody    Peroxidase conjugated anti-digoxygenin antibody b)

NON-CROSS-REACTIVE ANTI IGG ANTIBODIES

RELATED APPLICATIONS

This application is a 371 of Application No. PCT/EP2010/065617, filed Oct. 18, 2010, which claims priority to European Application number 09013144.2 filed Oct. 19, 2009.

Herein are reported antibodies specifically binding to the constant region of an IgG-Fab-fragment of human and chimpanzee antibodies of the IgG class and use thereof in immunoassays.

BACKGROUND OF THE INVENTION

Since the development of the first monoclonal antibodies by Koehler and Milstein in 1974, a lot of efforts have been dedicated to the development of antibodies which are appropriate for therapy in humans. The first monoclonal antibodies which became available had been developed in mice and rats. In the past ten years an ever growing number of human monoclonal antibodies or humanized monoclonal antibodies have reached the market. Well-known examples include for example Herceptin® and MabThera® from F. Hoffmann-La Roche AG, Basel.

A quite significant number of human or humanized monoclonal antibodies is under investigation and needs to be studied in experimental animals, before entry into human can be considered for the first trial purposes. Important criteria like bio-availability and antibody clearance just to mention two of them have to be studied.

Many of these studies require the quantification of the therapeutic antibody in the background of the experimental animal's own antibodies. In most cases mammals are used as experimental animals. Toxicology often is first assessed in rodents like mice or rats. In the more advanced stages of drug development, especially before entry of the drug into human beings, even monkeys have to be included into such pre-clinical studies.

Mammals usually have between about 10 to about 30 milligram of antibody per ml in the circulation. Therapeutic monoclonal antibodies typically have to be tested with serum levels ranging from about between 1 nanogram per ml to about 100 microgram per ml. The therapeutic antibody, thus, has to be detected against a background of experimental animal's antibodies which are in an excess of about 100-fold to 10 million-fold.

The detection of a human or humanized therapeutic antibody in the background of an experimental animal's antibody represents quite a significant task to the pharmacologist. The detection of a human or humanized antibody becomes more and more difficult the closer the test animal is related to *H. sapiens*.

In WO 2008/031532 an anti-drug antibody assay is reported. The detection of a therapeutic antibody in an experimental animal is reported in WO 2006/066912. In U.S. Pat. No. 5,332,665 species specific, high affinity monoclonal antibodies are reported.

SUMMARY OF THE INVENTION

Herein are reported at first a conformational epitope on antibodies of the immunoglobulin class G of humans and chimpanzee that is not present in commonly used experimental animals. At second are reported non-cross-reactive anti-human IgG antibodies and anti-chimpanzee IgG antibodies binding to this epitope. At third are reported assays using these antibodies.

One aspect as reported herein is an antibody binding to human or chimpanzee IgG (immunoglobulin of subclass G) and not binding to canine and marmoset IgG.

In one embodiment the antibody is not binding to canine, Rhesus-monkey, marmoset, baboon, and cynomolgus IgG. In another embodiment the antibody is specifically binding to human and chimpanzee IgG. In a further embodiment the $K_D$-value for binding to a human or chimpanzee IgG is $10^{-9}$ mol/l or less determined by surface plasmon resonance and the $K_D$-value for binding to canine, Rhesus-monkey, marmoset, baboon, and cynomolgus IgG is $10^{-6}$ mol/l or more. In one embodiment the $K_D$-value for binding to a human or chimpanzee IgG is of from $10^{-9}$ mol/l to $10^{-13}$ mol/l. In another embodiment the $K_D$-value for binding to canine, Rhesus-monkey, marmoset, baboon, and cynomolgus IgG is not determinable via surface plasmon resonance. In one embodiment the antibody is a monoclonal antibody.

Another aspect as reported herein is an antibody specifically binding to an IgG1 (immunoglobulin of subclass G1) that comprises a kappa light chain constant domain.

In one embodiment the antibody is further binding to an IgG2. In another embodiment the antibody is further binding to an IgG4. In another embodiment the antibody is not binding to an IgG3. In one embodiment the antibody is not binding to an IgG1 that comprises a lambda light chain constant domain. In one embodiment the antibody is a monoclonal antibody.

The herein reported antibodies obtained from cell lines DSM ACC3006 (M-1.3.2), DSM ACC3007 (M-1.5.8), and DSM ACC3008 (M-1.7.10) show a reduced cross-reactivity compared e.g. to antibody M-R10Z8E9 produced by cell line DSM ACC2708, bind to different epitopes in the Fab-region, are not influenced by a neighboring glycosylation site, and can be mixed in an immunoassay for the determination of Fab therapeutic antibodies as the binding sites of each of the antibodies is present only once in the Fab-fragment.

Individual aspects as reported herein are the cell lines DSM ACC3006, DSM ACC3007, and DSM ACC3008 as well as the respective antibodies obtained from the cell lines and the use of these antibodies in an immunoassay.

A further aspect is a kit comprising
a) an antibody obtained from cell line DSM ACC3006, or DSM ACC3007, or DSM ACC3008, or DSM ACC2708 in biotinylated form,
b) an antibody obtained from cell line DSM ACC3006, or DSM ACC3007, or DSM ACC3008, or DSM ACC2708 in digoxygenylated form.

Another aspect as reported herein is a method for detecting a therapeutic antibody in a sample obtained from an experimental animal comprising the steps of
a) providing the sample to be analyzed,
b) incubating the sample with an antibody binding to the same epitope as an antibody as reported herein,
c) optionally incubating the sample with a reagent appropriate for the selective detection of total, active or antigen-bound therapeutic antibody, and
d) correlating the complex formed in (b) or (c) to the concentration of the therapeutic antibody, optionally via a calibration curve.

Still another aspect as reported herein is a method for immunologically determining a therapeutic antibody in a sample obtained from an experimental animal using an antigen bridging immunoassay comprising a capture antibody and a tracer antibody, wherein the capture antibody and the tracer antibody are both independently selected from antibodies binding to the same epitope as an antibody as reported herein.

In one embodiment the immunoassay is a sandwich immunoassay. In another embodiment the conjugation of the antibody to its conjugation partner is performed by chemically binding via N-terminal and/or ε-amino groups (lysine), ε-amino groups of different lysines, carboxy-, sulfhydryl-hydroxyl- and/or phenolic functional groups of the amino acid backbone of the antibody and/or sugar alcohol groups of the carbohydrate structure of the antibody. In a further embodiment the capture antibody is immobilized via a specific binding pair. In one embodiment the capture antibody is conjugated to biotin and immobilization is performed via immobilized avidin or streptavidin. In still another embodiment the tracer antibody is conjugated to the detectable label via a specific binding pair. In one embodiment the tracer antibody is conjugated to digoxygenin and linking to the detectable label is performed via an antibody against digoxygenin. In another embodiment the therapeutic antibody is a Fab. In one embodiment the experimental animal is selected from the group comprising the members of the families of marmosets and tamarins, old world monkeys, dwarf and mouse lemurs, gibbons and lesser apes, true lemurs, as well as crossings thereof. In one embodiment the experimental animal is selected from dog, Rhesus-monkey, marmoset, baboon and cynomolgus. In one embodiment the experimental animal is a *Macaca* monkey. In a further embodiment the antibody binding to the therapeutic antibody and not binding to the immunoglobulin of the experimental animal is an antibody as reported herein. In one embodiment the therapeutic antibody is a human or a humanized antibody. In a further embodiment the human or humanized antibody is a monoclonal antibody. In one embodiment the total therapeutic antibody is detected, in another the active therapeutic antibody is detected, and in a further embodiment, the therapeutic antibody is detected which is bound to its antigen.

Another aspect as reported herein is the use of an antibody which is binding to a therapeutic antibody and not binding to the immunoglobulin of an experimental animal for determining the concentration of total, active, or antigen-bound therapeutic antibody in a sample obtained from an experimental animal whereby the antibody is binding to the same epitope as an antibody as reported herein. In one embodiment the antibody is an antibody as reported herein.

A further aspect as reported herein is an antibody composition comprising a mixture of the antibody produced by the cell line DSM ACC3006, the cell line DSM ACC3007, the cell line DSM ACC3008, and/or the cell line DSM ACC2708.

Also an aspect is the use of an antibody composition as reported herein in a method as reported herein.

DETAILED DESCRIPTION OF THE INVENTION

The non-cross-reactive anti-human IgG antibody denoted M-R10Z8E9 (obtained from the cell line DSM ACC2708) binds to an epitope in the CH2 domain of human immunoglobulin of class G near the glycosylation site Asn297. The herein reported antibodies M-1.3.2, M-1.5.8 and M-1.7.10 show a reduced cross-reactivity compared to antibody M-R10Z8E9, bind to a different epitope in the Fab-region, are not influenced by a neighboring glycosylation site, and can be mixed in an immunoassay for the determining of therapeutic antibodies, especially of Fab therapeutic antibodies, as the binding sites of each of the antibodies is present in the Fab-fragment.

The term "therapeutic antibody" denotes an antibody which is tested in clinical studies for approval as human therapeutic and which can be administered to an individual for the treatment of a disease. In one embodiment the therapeutic antibody is a monoclonal antibody. In a further embodiment the therapeutic antibody is selected from an antibody obtained from a great ape, an antibody obtained from an animal transformed with a human antibody locus, a human monoclonal antibody, or a humanized monoclonal antibody. In one embodiment the therapeutic antibody is a human monoclonal antibody. In a further embodiment the therapeutic antibody is a humanized monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, for instance, antibodies against CD20, CD22, HLA-DR, CD33, CD52, EGFR, G250, GD3, HER2, PSMA, CD56, VEGF, VEGF2, CEA, Lewis Y antigen, IL-6 receptor (IL6R), or IGF-1 receptor (IGF1R).

The term "antibody" encompasses the various forms of antibody structures including whole antibodies and antibody fragments. The antibody as reported herein is in one embodiment a human antibody, a humanized antibody, a chimeric antibody, or a T-cell antigen depleted antibody. Genetic engineering of antibodies is e.g. described in Morrison, S. L., et al, Proc. Natl. Acad Sci. USA 81 (1984) 6851-6855; U.S. Pat. No. 5,202,238 and U.S. Pat. No. 5,204,244; Riechmann, L., et al, Nature 332 (1988) 323-327; Neuberger, M. S., et al, Nature 314 (1985) 268-270; Lonberg, N., Nat. Biotechnol. 23 (2005) 1117-1125.

"Humanized" forms of non-human (e.g. rodent) antibodies are chimeric antibodies that contain partial sequences derived from a non-human antibody and from a human antibody. For the most part, humanized antibodies are derived from a human antibody (recipient antibody), in which residues from a hypervariable region are replaced by residues from a hypervariable region of a non-human species (donor antibody), such as mouse, rat, rabbit, or non-human primate, having the desired specificity and affinity. In some instances, framework region (FR) residues of the human antibody are replaced by corresponding non-human residues. Furthermore, humanized antibodies may comprise further modifications, e.g. amino acid residues that are not found in the recipient antibody or in the donor antibody. Such modifications result in variants of such recipient or donor antibody, which are homologous but not identical to the corresponding parent sequence. These modifications are made to further refine antibody performance.

In general, the humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally will also comprise at least a portion of an antibody constant region, typically that of a human antibody.

Methods for humanizing non-human antibodies have been described in the art. In one embodiment a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some hypervariable region residues and possibly some framework region residues are substituted by residues from analogous sites in rodent or non-human primate antibodies.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "experimental animal" as used herein denotes the members of the families of the order of primates comprising marmosets and tamarins (family Callitrichidae), new world monkeys (family Cebidae), old world monkeys (family Cercopithecidae, e.g. *Macaca* monkeys), dwarf and mouse lemurs (family Cheirogaleidae), aye-aye (family Daubentoniidae), bushbabies and galagos (family Galagonidae), gibbons and lesser apes (family Hylobatidae), indris, sifakas, and relatives (family Indridae), true lemurs (family Lemuridae), lorises (family Loridae), sportive lemurs (family Megaladapidae), tarsiers (family Tarsiidae), as well as crossings thereof.

In one embodiment the experimental animal is selected from the group comprising the members of the families of marmosets and tamarins, old world monkeys, dwarf and mouse lemurs, gibbons and lesser apes, true lemurs, as well as crossings thereof. In this embodiment the closest relatives to mankind, the great apes, especially the group of chimpanzees, bonobos, gorillas and orangutans is excluded.

The term "sample" denotes any tissue or liquid sample removed from an experimental animal. In one embodiment the sample will be a liquid sample like Saliva, urine, whole blood, plasma or serum. In a further embodiment the sample will be whole blood, plasma or serum.

An "antibody binding to a therapeutic antibody and not binding to the antibody of an experimental animal" will bind to a therapeutic antibody with a dissociation constant $(=K_{Diss})$ of at least $10^{-9}$ mol/l, in another embodiment with a $K_{Diss}$ of at least $10^{-10}$ mol/l. At the same time the property of not binding to the antibody of the experimental animal is insured by a $K_{Diss}$ of $10^{-7}$ mol/l or worse. Also in one embodiment the antibody binding to a therapeutic antibody and not binding to the antibody of an experimental animal will have a $K_{Diss}$-gap of at least 100-fold between its reactivity towards the immunoglobulin of class G of an experimental animal and towards human or chimpanzee immunoglobulin of class G, respectively.

Generally, the term "binding to" denotes that an antibody binds to its antigen or the corresponding antibody receptor, whichever is intended in the respective context, with a dissociation constant of $(=K_D=K_{Diss})$ $10^{-9}$ mol/l or less, in another embodiment with a $K_D$ of at least $10^{-10}$ mol/l. At the same time the property of not binding is insured by a $K_D$ of $10^{-7}$ mol/l or more (e.g. $10^{-5}$ mol/l). Also in one embodiment the antibody binding to a first antibody and not binding to a second antibody will have a $K_D$-gap of at least 100-fold between its reactivity towards the first immunoglobulin of class G and towards the second immunoglobulin of class G.

The binding properties of an antibody, especially the $K_{Diss}$, in one embodiment are assessed by surface plasmon resonance on a BIAcore® instrument. In this method binding properties are evaluated by changes in surface plasmon resonance (SPR). It is convenient to bind the antibody under investigation to the solid phase (called chip) and to assess binding of a monoclonal antibody, a polyclonal antibody or even of serum comprising IgG to this coated chip.

The antibody binding to a therapeutic antibody and not binding to the antibody of the experimental animal under investigation may be a monoclonal antibody, fragments of such antibodies, as well as genetic constructs comprising the binding domain of such an antibody. Any antibody fragment retaining the above criteria of binding to the therapeutic antibody and of non-binding to the antibody of the experimental animal can be used.

Various aspects connected to the application of a therapeutic antibody in an experimental animal may have to be assessed during pre-clinical studies. In certain settings it may be relevant to analyze the total amount of therapeutic antibody present, or it may be important to analyze certain fragments of a therapeutic antibody, or certain modifications of a therapeutic antibody, or the concentration of therapeutic antibody bound to an antigen, or the fraction of a therapeutic antibody still capable of binding to an antigen. In one embodiment the antibodies and methods as reported herein can be used to detect the total, active, or antigen-bound therapeutic antibody, respectively.

The term "total therapeutic antibody" denotes any antibody detected irrespective of whether the antibody is active (i.e. still reactive with its antigen), inactive, and/or antigen-bound.

The term "active therapeutic antibody" denotes the therapeutic antibody present in an experimental animal that still is capable of binding its antigen. Such antibodies, e.g., have not bound its antigen or any other molecule at its antigen binding site.

The term "antigen-bound therapeutic antibody" denotes the therapeutic antibody as present in the circulation of an experimental animal that is bound to its antigen.

Total, active, or antigen-bound therapeutic antibody as defined above can be directly detected with the antibodies and in methods as reported herein.

Additionally it is possible to detect other forms of non-active therapeutic antibodies, such as therapeutic antibodies bound by anti-drug antibodies or antiidiotype antibodies or especially neutralizing anti-drug antibodies.

In addition, it is also possible to indirectly assess any "inactive therapeutic antibody". Such inactive therapeutic antibody may, e.g., be a therapeutic antibody bound to its antigen, or the therapeutic antibody bound to a cross-reactive antigen, or the therapeutic antibody blocked by an auto or anti-idiotypic antibody against the therapeutic antibody. In case the total antibody amounts to more than the sum of active antibody and antigen-bound antibody, an additional fraction of antibody comprising the inactive antibody not bound to its corresponding antigen will be present.

Total therapeutic antibody for example can be detected in a so-called competitive immunoassay system or in a so-called sandwich type assay system. Such assay may be performed in one embodiment without washing steps (homogeneous immunoassay) or in another embodiment with washing steps (heterogeneous immunoassay).

In one embodiment the total therapeutic antibody is detected in a sandwich type immunoassay, wherein the antibody which is binding to a therapeutic antibody and not binding to the antibody of the experimental animal is used at both sides of such a sandwich assay. The antibody used at one side of such sandwich is bound or capable of binding to a solid phase (often referred to as capture antibody), whereas the antibody at the other side of such sandwich is labeled in such a manner that direct or indirect detection is facilitated (so-called detection antibody). The amount of detection antibody bound in such a sandwich assay procedure is directly correlated to the amount of therapeutic antibody in the sample investigated.

Detection of active therapeutic antibody in a sample may be achieved by convenient state of the art procedures. However, the detection of total therapeutic antibody or of the fraction of therapeutic antibody bound to its antigen is rather complicated and requires quite different assay set-ups and especially requires tailor-made reagents for each of the different assays. With the antibodies as reported herein which are binding to a therapeutic antibody and not binding to the antibody of the experimental animal it is possible to assess the fraction of active therapeutic antibody, total therapeutic antibody, or antigen-bound therapeutic antibody in test systems which are analogues to each other. This kind of comparative assessment of total, active, or antigen-bound therapeutic antibody should have advantages once quantitative comparisons are made in between these various fractions of therapeutic antibody.

In one embodiment a sandwich type assay format is set up to detect the active therapeutic antibody. In a further embodiment the antibody which is binding to a therapeutic antibody and not binding to the antibody of the experimental animal is used as a capture antibody and the detection side of such sandwich assay either makes use of the antigen in a labeled form or after binding of the antigen makes use of a second antibody not binding to or competing with the epitope recognized by the therapeutic antibody, wherein the second antibody is specifically detectable and/or is labeled in such a manner that direct or indirect detection is facilitated.

The antigen-bound therapeutic antibody in one embodiment is detected in a sandwich type assay format using the antibody binding to a therapeutic antibody and not binding to the antibody of the experimental animal as a capture reagent. In the detection in one embodiment a second antibody is used binding to the antigen at an epitope which does not compete with the epitope of the therapeutic antibody. The second antibody is in one embodiment labeled in such a manner that direct or indirect detection is facilitated.

For direct detection the labeling group can be selected from any known detectable marker groups, such as dyes, luminescent labeling groups such as chemo luminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay), and radioisotopes. Metal chelates which can be detected by electrochemoluminescence are also in one embodiment signal-emitting groups used as detectable labels, with particular preference being given to ruthenium chelates. In one embodiment the labeling group is a ruthenium (bispyridyl)$_3^{2+}$ chelate.

Indirect detection systems comprise, for example, that the detection reagent, e.g. the detection antibody, is labeled with a first partner of a binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. In one embodiment the first binding pair member is selected from hapten, antigen and hormone. In one embodiment the hapten is selected from digoxin and biotin and analogues thereof. The second partner of such binding pair, e.g. an antibody, streptavidin, etc., usually is labeled to allow for direct detection, e.g., by the labels as mentioned above.

In all the above immunological detection methods reagent conditions are chosen which allow for binding of the reagents employed, e.g. for binding of an antibody to its corresponding antigen. The skilled artisan refers to the result of such binding event by using the term complex. The complex formed in an assay method as reported herein is correlated by state of the art procedures to the corresponding concentration of the therapeutic antibody. Such a correlation can be made e.g. by way of preparing and determining the complex in a dilution series of the corresponding complex with the method as reported herein and by correlating the obtained result with the concentration of the individual complex components. Depending on the detection reagent employed this correlating step will result in the concentration of total, active, or antigen-bound therapeutic antibody.

As the skilled artisan will appreciate the methods as reported herein will not only reveal the concentrations of total, antigen-bound, active or even inactive therapeutic antibody. Due to the use of one and the same reagent, the antibody binding to a therapeutic antibody and not binding to the antibody of the experimental animal, in the different assays the values obtained can be easily compared to each other and even ratios thereof assessed. In a further embodiment the present method relates to the ratio of active to total therapeutic antibody. This ratio may well serve as an indicator for the efficacy of a therapeutic antibody.

During the course of the experiments it has been found that one or more epitope(s) that is (are) present on all classes of human and chimpanzee antibody of class G are not present on the antibody of any experimental animal. This (these) epitope(s) is (are) characterized by its binding to the antibodies produced by the deposited cell lines DSM ACC3006, DSM ACC3007, DSM ACC3008. Therefore, one aspect reported herein is an antibody produced by the cell line DSM ACC3006, or DSM ACC3007, or DSM ACC3008.

As the epitope(s) recognized by the three deposited cell lines is (are) unique in the Fab region of an antibody another aspect as reported herein is (are) the epitope(s) binding to the antibodies obtained from the deposited cell lines DSM ACC3006, DSM ACC3007, DSM ACC3008. In one aspect as reported herein the antibody binding to a therapeutic antibody and not binding to the antibody of an experimental animal is characterized in that the antibody is an antibody binding to the same epitope as one of the antibodies produced by the cell lines DSM ACC3006, DSM ACC3007, and DSM ACC3008.

For example, a method can be used in which epitope overlapping of two antibodies binding to the same target antigen is determined with the help of a competitive test system. For this purpose, for example with the help of an enzyme immunoassay, there is tested the extent to which the antibody in question competes with the known antibody for the binding to an immobilized target antigen, e.g. employing an antibody produced by one of the cell lines as reported herein. For this purpose, an appropriately immobilized target antigen is incubated with the known antibody in labeled form and an excess of the antibody in question. By detection of the bound labeling there can easily be ascertained the extent to which the antibody in question can displace the known antibody from the binding. If there is a displacement of more than 20%, in another embodiment of more than 30%, at the same concentration or a displacement of more than 70%, in another embodiment of more than 80%, at higher concentrations, in one embodiment in the case of $10^3$-$10^5$-fold excess of the antibody in question, referred to the known antibody, then epitope overlapping is present and both antibodies bind to the same or an overlapping part of the same epitope.

The specificity of the antibodies obtained from the deposited cell lines DSM ACC3006, DSM ACC3007, and DSM ACC3008 can be shown in a sandwich-ELISA employing each a biotinylated and a digoxygenylated variant of the respective antibodies and serum from different species. In the assay (see FIG. 1a)), capture and detection antibodies are obtained from the same cell line binding to identical epitopes. To be a generally applicable assay for detection and quantification of human IgG in the serum of an experimental animal, such an assay requires an anti-human IgG antibody whose binding site is independent from any secondary antibody modification, such as e.g. glycosylation or deamidation. Otherwise it would be necessary to optimize the assay for each new therapeutic antibody to be detected and quantified. Furthermore, each of the herein reported anti-human IgG antibodies is also different to the analyzed therapeutic antibody and can be employed as reference standard and positive control. Specificity results obtained with this assay are shown in FIG. 2.

It can be seen that the antibodies as reported herein are highly specific for human and chimpanzee immunoglobulin of the immunoglobulin class G and show a better specificity than the antibody M-R10Z8E9 and do not bind to the immunoglobulin of class G of an experimental animal. All values of the experimental animals are well below a blank value obtained with ABTS without peroxidase present.

The specificity of the antibodies as reported herein can also be shown in a surface plasmon resonance experiment using the BIAcore technology. In FIGS. 3a)-3c) the BIAcore diagrams of the antibodies M-1.7.10 (obtained from DSM ACC3008), M-1.3.2 (obtained from DSM ACC3006), and M-1.5.8 (obtained from DSM ACC3007) are shown from which can be seen that the antibodies are specific for human and chimpanzee immunoglobulin of class G.

By using dot-blot experiments it has been shown that the epitope(s) bound by the antibodies as reported herein is (are) a conformational epitope as binding is lost denatured human immunoglobulin (FIG. 4).

Another aspect as reported herein is an assay for quantifying a human antibody or its derivative such as Fab-fragments in a sample obtained from an experimental animal comprising a biotinylated antibody as reported herein as capture antibody and a digoxygenylated antibody as reported herein as tracer antibody. In FIGS. 5a) and 5b), the schematic assay set-up and a calibration curve for this assay with exemplary antibodies as reported herein, respectively are shown (capture antibody: biotinylated M-1.7.10, analyte: Fab-fragment of human anti-IL13Rα1 antibody, tracer antibody: digoxigenylated M-1.3.2). This assay requires capture and tracer antibodies which bind to the Fab fragment of human IgG on two different epitopes. The herein reported antibodies bind at least partially to the constant light chain domain of a human or chimpanzee antibody of the immunoglobulin class G and are therefore well suited for this assay.

Another aspect as reported herein is an assay comprising a capture and tracer antibody binding specifically to epitopes on different domains of a human IgG. In this assay only an intact therapeutic antibody will result in a positive assay result and a detectable signal. In one embodiment the capture antibody and the tracer antibody are independently selected from the antibodies as reported herein on the one hand and the antibody M-R10Z8E9 on the other hand. An exemplary assay according to this aspect, used to prove the structural integrity of a human IgG in an experimental animal, employs 1) as capture antibody, biotinylated M-R10Z8E9, 2) as analyte, an anti-IL13Rα1 antibody, and 3) as tracer antibody, digoxygenylated M-1.3.2 (in FIGS. 6a) and 6b), the schematic assay set-up, and a calibration curve for this assay, respectively are shown).

A further aspect as reported herein is an assay in which the anti-human IgG antibody is used as a reference standard and/or positive control to mimic an anti drug antibody (ADA). This can be useful during assay development to find out optimal assay conditions and test robustness of the assay, i.e. to check assay performance with different standard reagents/positive controls. Especially advantageous is this set-up in view of the fact that an ADA will be polyclonal and probably be directed against both, the Fab fragment and the Fc part.

In a further aspect as reported herein one of the antibodies obtained from the cell lines DSM ACC3006, DSM ACC3007, and DSM ACC3008 is used as the antibody binding to a therapeutic antibody and not binding to the antibody of the experimental animal in a method as reported herein.

A further aspect as reported herein relates to the use of an antibody which is binding to a therapeutic antibody and not binding to the antibody of an experimental animal for measuring the concentration of total, active, or antigen-bound therapeutic antibody in a sample obtained from an experimental animal. In one embodiment the antibody used in such method is selected from an antibody binding to the same or an overlapping epitope as recognized by one of the antibodies obtained from the cell line DSM ACC3006, DSM ACC3007, or DSM ACC3008.

A further aspect as reported herein relates to the use of two antibodies which both are binding to a therapeutic antibody and not binding to the antibody of an experimental animal for measuring the concentration of total, active, or antigen-bound therapeutic antibody in a sample obtained from an experimental animal, wherein one of the antibodies is the capture antibody and one of the antibodies is the tracer antibody. In one embodiment the therapeutic antibody is a Fab fragment.

Alternatively the antibodies as reported herein can be used in a conjugate comprising as one part a reference immunoglobulin of a single immunoglobulin class. The reference immunoglobulin provides an immunoglobulin class specific constant region that can be specifically bound by an anti-immunoglobulin-class antibody, such as an anti-human-immunoglobulin-G antibody. Thus, the reference immunoglobulin provides such a conjugate with an immunoglobulin class specific tag, which can be specifically identified by a tag specific antibody. For example, if the tag is an immunoglobulin G constant region a tag specific antibody is an anti-immunoglobulin-G antibody. Such a conjugate can be used as a standard in an immunoassay or as a positive control in an immunoassay.

In these methods, different capture molecules can be used, such as complete antibodies, F(ab')$_2$ fragments, Fab fragments or even single chain antibodies.

The preferred hybridoma cell lines as reported herein, MAK<H-IgG>M-1.3.2, MAK<H-IgG>M-1.5.8, and MAK<H-IgG>M-1.7.10, expressing antibodies M-1.3.2, M-1.5.8, and M-1.7.10, respectively, were deposited, under the Budapest Treaty on the international recognition of the deposit of microorganisms for the purposes of patent procedure, with Deutsche Sammlung von Mikroorganismen and Zellkulturen GmbH (DSMZ), Inhoffenstr. 7 B, D-38124 Braunschweig, Germany:

| Cell line | Deposition No. | Date of Deposit |
| --- | --- | --- |
| MAB<h-Fc gamma>M-R10Z8E9 | DSM ACC2708 | 22 Dec. 2004 |
| MAK<H-IgG>M-1.3.2 | DSM ACC3006 | 24 Sep. 2009 |
| MAK<H-IgG>M-1.5.8 | DSM ACC3007 | 24 Sep. 2009 |
| MAK<H-IgG>M-1.7.10 | DSM ACC3008 | 24 Sep. 2009 |

The cell lines and antibodies obtainable from said cell lines are aspects as reported herein.

The methods reported herein are exemplified with an antibody against the IL13 receptor α1 protein (anti-IL13Rα1 antibody) as reported in WO 2006/072564, an antibody against the IL-1R receptor (anti-IL1R antibody) as reported in WO 2005/023872, an antibody against the amyloid β-A4 peptide (anti-Aβ antibody) as reported in WO 2003/070760 or US 2005/0169925, an antibody against the human P-Selectin glycoprotein (anti-P Selectin antibody) as reported in WO 2005/100402, or US 2005/0226876, an antibody against the IL-6 receptor (anti-IL6R antibody) as reported in WO 2004/096274, and an antibody against the IGF-1 receptor (anti-IGFIR antibody) as reported in WO 2004/087756 or in WO 2005/005635 (all incorporated herein by reference).

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1a) assay format.

FIG. 3a) M-1.3.2, FIG. 3b) M-1.5.8, and FIG. 3c) M-1.7.10 as reported herein.

FIG. 5a) schematic assay set-up, FIG. 5b) calibration curve.

FIG. 6a) schematic assay set-up, FIG. 6b) calibration curve.

EXAMPLE 1

Figure 1:
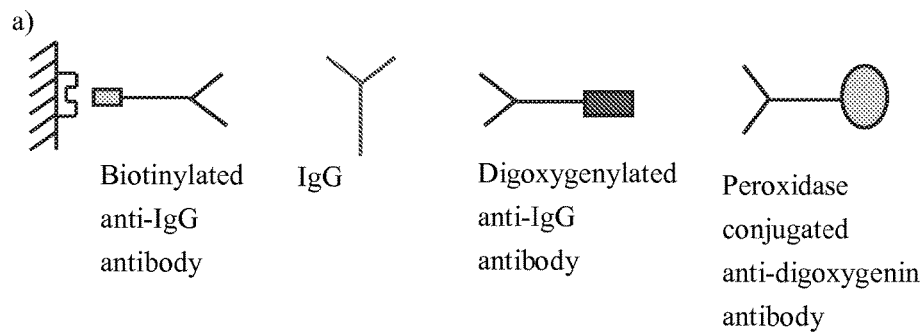
FIGS. 1a)-1c) Fully generic Assay for quantification of human antibodies (human IgG) in an experimental animal.
FIG. 1b) capture and detection reagent: antibody M-R10Z8E9.
FIG. 1c) capture and detection reagent antibody M-1.7.10; therapeutic antibodies: empty triangles: anti-IL13Rα1 antibody, empty squares: anti-Abeta antibody, solid squares: anti-IL1R antibody, solid triangles anti-IL6R antibody.
Figure 1:
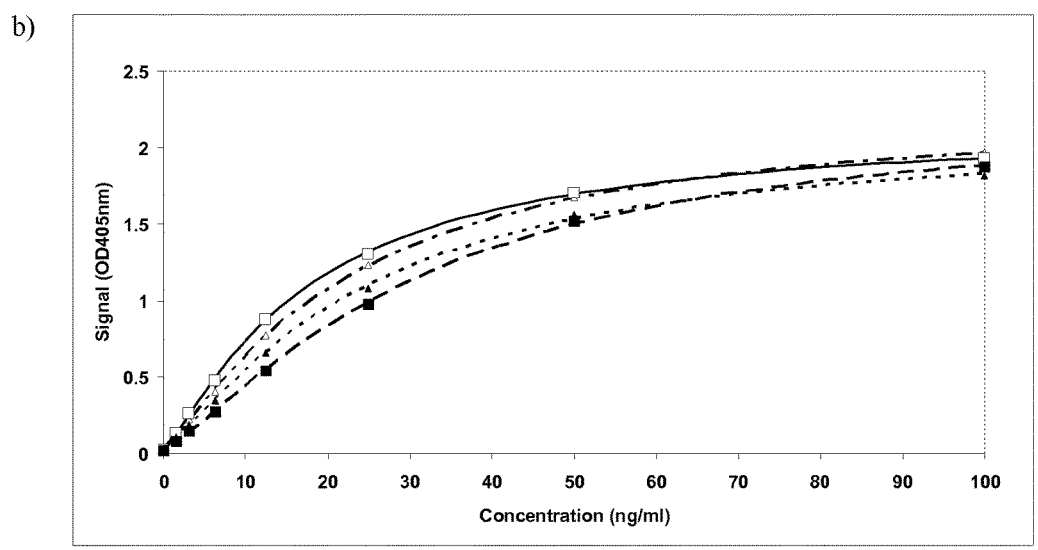
Figure 1:
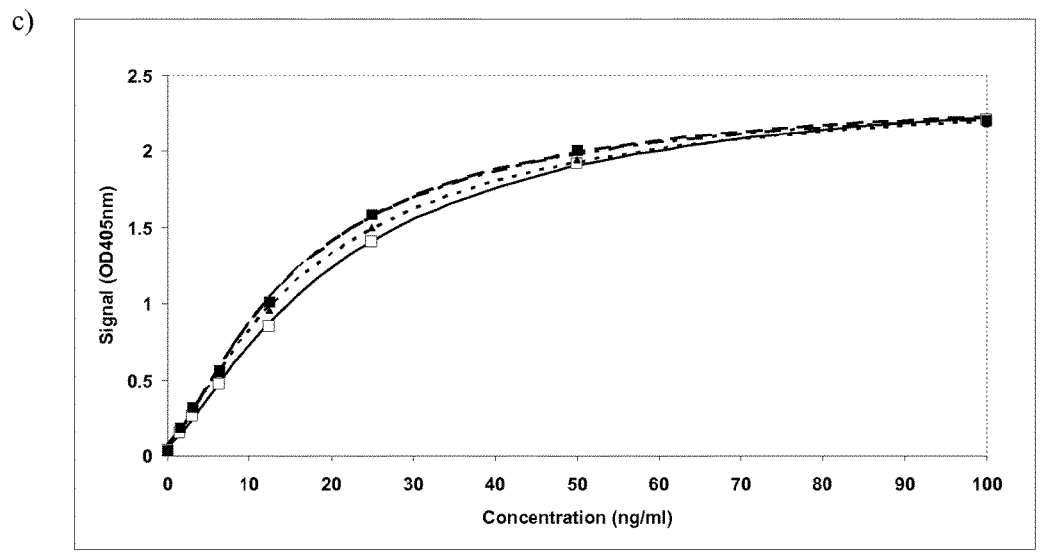
Figure 2:
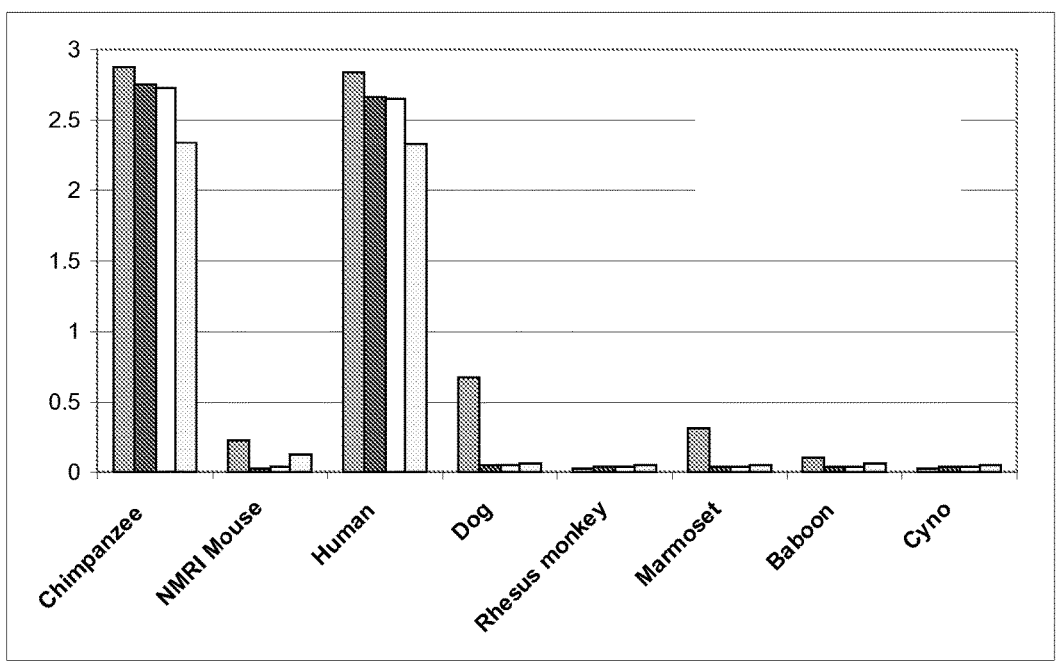
FIG. 2 Results obtained with an assay employing the antibodies as reported herein; antibodies used from left to right: M-R10Z8E9, M-1.3.2, M-1.5.8, M-1.7.10.

Preparation of the F(Ab')$_2$ Fragment of Human IgG (Immunogen)

The full length human antibody of the class G (human IgG) in 100 mM sodium citrate buffer, pH 3.7 was incubated with pepsin (1 µg pepsin per mg IgG). The fragmentation was analyzed by analytical gel filtration and stopped after 90 minutes by adjusting the pH value to 6.5 by the addition of potassium phosphate. After dialysis of the mixture against 10 mM sodium citrate buffer with 10 mM sodium chloride, pH 5.5, the solution was applied to an SP-Sepharose® chromatography column and the isolated fractions eluted in a salt gradient were analyzed individually by analytical gel filtration. The pool containing the antibody F(ab')$_2$ fragments were applied to an affinity matrix with immobilized polyclonal antibodies against human Fcγ to eliminate trace amounts of Fcγ fragments. The flow through was pooled, concentrated to about 16 mg/ml and finally applied to a gel filtration column (Superdex® 200).

EXAMPLE 2

Generation of Monoclonal Anti-Human IgG Antibodies a) Immunization of Mice

Female NMRI mice, 8-12 weeks of age, were each primarily immunized intraperitoneally with 100 µg of the antibody F(ab')$_2$ fragments prepared according to Example 1 mixed with CFA (Complete Freund's Adjuvant). Two further intraperitoneal immunization steps followed after 6 and 10 weeks, each with 100 µg of the antibody F(ab')$_2$ fragments per mouse mixed with IFA (Incomplete Freund's adjuvant). Subsequently, intravenous boost immunizations were done, each with 50 µg of antibody F(ab')$_2$ fragments in PBS (phosphate buffered saline) three days before the fusion.

b) Fusion and Cloning

Spleen cells of the mice immunized according to a) were fused with myeloma cells according to Galfre and Milstein (Galfre, G. and Milstein, C, Methods Enzymol. 73 (1981) 3-46). Approximately 2.1×10$^8$ splenocytes were mixed with 4.2×10$^7$ myeloma cells (P3x63-Ag8.653, ATCC® CRL1580) and centrifuged (10 min. at 300×g and 4° C.). The cells were washed afterwards once with the culture medium PvPMI 1640 without FCS (fetal calf serum), and centrifuged again at 400×g in a 50 ml pointed vial. Thereafter, 1 ml of PEG (poly (ethylene glycol), molecular weight 4,000 g/mol) was added, mixing was done by the pipetting. After 1 min. in a water bath at 37° C., 5 ml of RPMI 1640 without FCS were added drop wise, the suspension was mixed, RPMI 1640 with 10% (v/v) FCS was added to a final volume of 50 ml, and then centrifuged. The sedimented cells were resuspended in RPMI 1640 with 10% FCS, and plated in hypoxanthine-azaserine selection medium (100 mmol/l hypoxanthine, 1 µg/ml azaserine in RPMI 1640 with 10% FCS) containing the growth factor recombinant murine interleukin 6 (Peprotech, 0.5 ng/ml). After 11 days, the primary cultures were assayed for specific antibody synthesis (see Example 3). Primary cultures exhibiting binding to biotinylated antibody F(ab')$_2$ fragments as well as to biotinylated human normal IgG were individualized by single cell deposition into 96-well cell culture plates using a flow cytometer (FACSAria™, BD Biosciences) in medium containing the growth factor recombinant murine interleukin 6 (Peprotech, 0.5 ng/ml). By following this protocol, the cell lines DSM ACC3006, DSM ACC3007, and DSM ACC3008 were obtained. Antibody M-1.7.10 is of the IgG2a class, antibodies M-1.5.8 and M-1.3.2 are of the IgG1 class.

c) Production of Immunoglobulin

The hybridoma cell lines obtained in b) were inoculated at initial cell densities (live cells) between $1.0 \times 10^5$ and $2.2 \times 10^5$ cells per ml in RPMI 1640 supplemented with 10% FCS, and commonly used supplements and expanded in a T-flask (Celline, IBS) for a period of approximately three weeks. In the harvested culture supernatants, concentrations between 0.7 mg/ml and 1.5 mg/ml of monoclonal antibody were obtained. Purification of the antibodies from the culture supernatants was done according to standard protein chemical methods, e.g. as those reported in Bruck, C., et al, Methods Enzymol. 121 (1986) 587-596.

EXAMPLE 3

Screening Assays for Detection of Anti-Human IgG Antibodies a) Primary Screening for Antibodies Binding to Human IgG For the determination of the specificity of the antibodies in the culture supernatants of the hybridoma cells, MTPs (microtiter plates) pre-coated with recombinant streptavidin (MicroCoat, Bernried, lot MC 1098) were coated with biotinylated humanized IgG used for the immunization process, 250 ng/ml, or biotinylated human IgG, 250 ng/ml, respectively, in PBS supplemented with 1% (w/v) BSA II (100 µl per well, 60 min. incubation at ambient temperature, with shaking), and subsequently washed three times with 0.9% (w/v) NaCl/0.05% Tween® 20. In the next step, per well 100 µl of the antibody solution to be assayed (culture supernatant) were added, and incubated for 60 min. at ambient temperature, with shaking. After three wash steps with 0.9% (w/v) NaCl/0.05% Tween® 20 per well, 100 µl of a horseradish peroxidase-labeled F(ab')$_2$ fragment of a polyclonal sheep anti-mouse Fcγ antibody were added for the detection of bound sample antibody, and incubated for 60 min. at ambient temperature, with shaking. Subsequently, washing was performed as above. Finally, 100 µl per well of ABTS® (Roche Diagnostics GmbH, Mannheim, Germany; catalog no. 1684302) were added. After 30 min. incubation at ambient temperature, the extinction (OD) was measured at 405 and 492 nm [405/492] in a commercial microtiter plate ELISA Reader. This screening led to a selection of antibodies binding well to humanized IgG as well as to human IgG. This selection of antibodies was further subjected to assay b).

b) Selection of Antibodies with Minimal Cross-Reactivity to IgG of Other Species Biotinylated human IgG was bound to the wells of a streptavidin-coated microtiterplate (SA-MTP) in the first step. The excess of unbound antibody was removed by washing. Afterwards the samples and the reference standards (e.g. anti-human IgG antibody as obtained with Example 2) were diluted in buffer and 10% cynomolgus serum. Diluted samples were added to the plate and incubated for 60 min. at ambient temperature, with shaking. After having washed away unbound substances, the human IgG of the first step in digoxygenylated form was added to the wells of the plate and incubated for another 60 min. After washing, the bound digoxygenylated antibody was detected with an anti-digoxygenin antibody-HRP conjugate. The HRP (horseradish peroxidase) of the antibody-enzyme conjugates catalyzes the color reaction of ABTS substrate. The signal is measured by ELISA reader at 405 nm wavelength (reference wavelength: 490 nm). Absorbance values of each serum sample were determined in triplicates.

Figure 7:
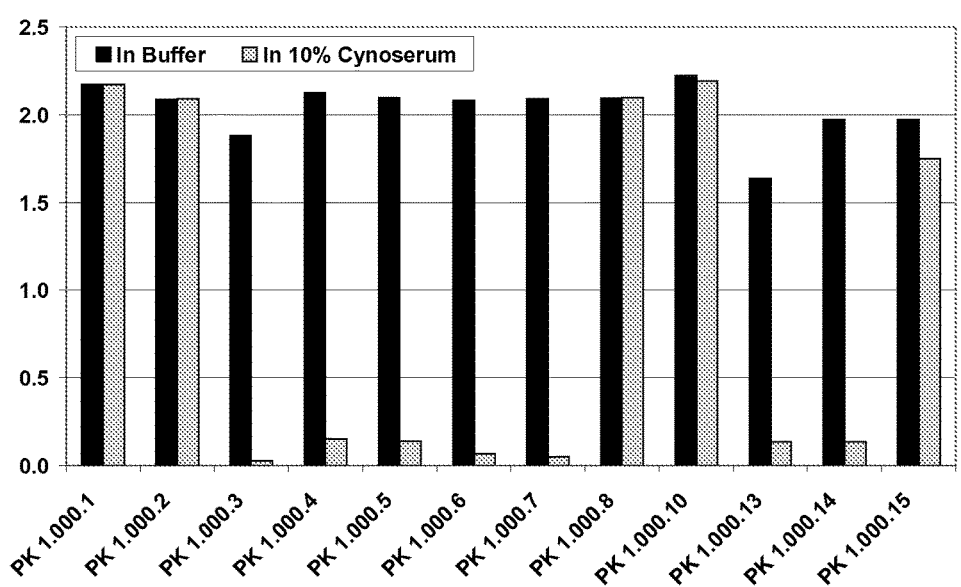
FIG. 7 Selection of antibodies with no detectable cross-reactivity to cynomolgus serum.

Antibodies with high assay response in cynomolgus serum as well as in buffer were selected (see FIG. 7). This second screening led to a selection of antibodies binding well to human IgG with minimal cross-reactivity to IgG of other species.

EXAMPLE 4

Assessment of Antibody Binding/Specificity by Surface Plasmon Resonance

All measurements were performed with the BIAcore® T100 instrument using a CM5-chip. Coating of this chip with an antibody was achieved by standard amine coupling. Unless otherwise indicated, all incubations were performed in HBS-buffer (HEPES, NaCl, pH 7.4) at 25° C. A saturating amount of a polyclonal goat anti-mouse Fc-gamma antibody was immobilized by amine coupling on one flow cell of the CM5-chip. Subsequently, the different monoclonal mouse antibodies directed against human IgG were injected for 60 seconds at a flow rate of 30 µl/min and were bound by the anti mouse Fc antibody. All animal sera were diluted in HBS buffer. Binding was analyzed by injection of the 1 in 100 diluted sera and incubation for 60 sec. at a flow rate of 30 µl/min. Dissociation was measured by washing the chip surface with HBS buffer for 180 sec. Using BIAevaluation Software from BIAcore® the dissociation constant values ($=K_D$) were calculated with a 1:1 Langmuir fitting model. For all animal sera this calculation was based on the assumption that the IgG level is 15 mg/ml. The signal values 80 sec. after start of the injection of the test antibody were chosen for the comparison of the amount of IgG bound (see Table 1).

TABLE 1

Binding signals [RU] and $K_D$-values for binding of animal sera to different monoclonal anti-human IgG antibodies.

| | Antibody | | | |
| --- | --- | --- | --- | --- |
| | M-R10Z8E9 | | M-1.3.2 | |
| Sample (serum) | Bound RU | $K_D$ mol/l | Bound RU | $K_D$ mol/l |
| Chimpanzee | 159 | $2.21 \times 10^{-10}$ | 95.7 | $1.12 \times 10^{-09}$ |
| Human | 151.3 | $1.77 \times 10^{-10}$ | 80.1 | $1.43 \times 10^{-09}$ |
| Dog | 35.5 | $3.17 \times 10^{-8}$ | −1.9 | no binding |
| Rhesus-monkey | −1.9 | no binding | −2.3 | no binding |
| Marmoset | 18.9 | $2.04 \times 10^{-7}$ | −2 | no binding |

TABLE 1-continued

Binding signals [RU] and $K_D$-values for binding of animal sera to different monoclonal anti-human IgG antibodies.

| Baboon | −1.5 | no binding | −2.2 | no binding |
| Cynomolgus | −1.4 | no binding | −2 | no binding |

| | Antibody | | | |
| --- | --- | --- | --- | --- |
| | M-1.5.8 | | M-1.7.10 | |
| Sample (serum) | Bound RU | $K_D$ mol/l | Bound RU | $K_D$ mol/l |
| Chimpanzee | 109.4 | $1.29 \times 10^{-09}$ | 109.4 | $1.94 \times 10^{-09}$ |
| Human | 77 | $1.43 \times 10^{-09}$ | 77 | $7.55 \times 10^{-09}$ |
| Dog | −2.4 | no binding | −2.4 | no binding |
| Rhesus-monkey | −2.7 | no binding | −2.7 | no binding |
| Marmoset | −2.1 | no binding | −2.1 | no binding |
| Baboon | −2.1 | no binding | −2.1 | no binding |
| Cynomolgus | −2.1 | no binding | −2.1 | no binding |

Table 1 shows that the three anti-human IgG antibodies do not cross-react with serum from other species except Chimpanzee. In contrast, for M-R10Z8E9 an additional interaction with serum from dog and marmoset was detected.

EXAMPLE 5 a) Purification of Mouse Monoclonal Anti-Human IgG Antibody

The fermentation supernatant of the cell lines obtained in Example 2 was concentrated about tenfold and transferred to a buffer with 20 mM TRIS, 1 M ammonium sulfate, pH 9.0, and applied to a protein A-Sepharose® chromatography column. The eluate obtained with 0.2 M sodium citrate, 0.2 M ammonium sulfate at pH 5.0 was dialyzed against phosphate buffer, pH 7.5. Contaminants of bovine IgG (from FCS in the fermentation broth) were separated by immunoadsorption with immobilized antibodies against bovine IgG.

b) Preparation of Biotinylated Anti-Human IgG Antibody

The anti-human IgG antibody obtained in a) in phosphate buffer, pH 8.5, was adjusted to a protein concentration of about 5 mg/ml. D-biotinoyl-aminocaproic acid-N-hydroxysuccinimide was dissolved in DMSO and added to the antibody solution in a molar ratio of 1:5. The reaction was stopped after 60 min. by adding L-lysine, and the surplus of the labeling reagent was removed by dialysis against 50 mM potassium phosphate buffer, with 150 mM NaCl, pH 7.5.

c) Preparation of Digoxigenylated Anti-Human IgG Antibody

The anti-human IgG antibody obtained in a) in phosphate buffer, pH 8.5, was adjusted to a protein concentration of about 5 mg/ml. Digoxigenin 3-O-methylcarbonyl-ε-aminocaproic acid-N-hydroxysuccinimide was dissolved in DMSO and added to the antibody solution in a molar ratio of 1:4. The reaction was stopped after 60 min. by adding L-lysine, and the surplus of the labeling reagent was removed by dialysis against 50 mM potassium phosphate buffer, with 150 mM NaCl, pH 7.5.

EXAMPLE 6

Fully Generic Assay for Quantification of Human Antibodies (Human IgG) in a Sample from an Experimental Animal Biotinylated antibody M-R10Z8E9 (plate 1) or antibody M-1.7.10 (plate 2) was bound to streptavidin-coated microtiter plates (SA-MTP) in the first step. The excess of unbound antibody was removed by washing. Samples/standards, e.g. anti-IL1R antibody, anti-IL13Rα1 antibody, anti-Abeta antibody and anti-IL6R antibody, spiked in cynomolgus serum were added in a concentration series to the plate and incubated for 60 min. at ambient temperature, with shaking. After having washed away unbound antibodies, 100 µl digoxygenylated antibody M-R10Z8E9 (plate 1) or antibody M-1.7.10 (plate 2) was added to the plate. After washing, the bound digoxygenylated antibodies were detected with an anti-digoxygenin-antibody-HRP conjugate. Absorbance values of each serum sample were determined in triplicates (see FIG. 1b) for plate 1 and FIG. 1c) for plate 2).

TABLE 2

OD data for capture and detection reagent antibody M-R10Z8E9.

| ng/ml | anti-IL13Rα1 antibody | anti-Abeta antibody | anti-IL1R antibody | anti-IL6R antibody |
| --- | --- | --- | --- | --- |
| 0.00 | 0.022 | 0.023 | 0.024 | 0.024 |
| 1.56 | 0.119 | 0.139 | 0.085 | 0.105 |
| 3.13 | 0.226 | 0.264 | 0.153 | 0.190 |
| 6.25 | 0.408 | 0.482 | 0.276 | 0.348 |
| 12.50 | 0.772 | 0.881 | 0.546 | 0.664 |
| 25.00 | 1.229 | 1.310 | 0.980 | 1.084 |
| 50.00 | 1.672 | 1.707 | 1.521 | 1.565 |
| 100.00 | 1.967 | 1.927 | 1.877 | 1.819 |

TABLE 3

OD data for capture and detection reagent antibody M-1.7.10.

| ng/ml | anti-IL13Rα1 antibody | anti-Abeta antibody | anti-IL1R antibody | anti-IL6R antibody |
| --- | --- | --- | --- | --- |
| 0.00 | 0.038 | 0.036 | 0.035 | 0.037 |
| 1.56 | 0.178 | 0.149 | 0.187 | 0.181 |
| 3.13 | 0.325 | 0.264 | 0.326 | 0.312 |
| 6.25 | 0.570 | 0.472 | 0.568 | 0.540 |
| 12.50 | 1.004 | 0.853 | 1.013 | 0.955 |
| 25.00 | 1.592 | 1.407 | 1.588 | 1.498 |
| 50.00 | 1.995 | 1.923 | 2.013 | 1.947 |
| 100.00 | 2.197 | 2.213 | 2.209 | 2.185 |

EXAMPLE 7

Figure 5:
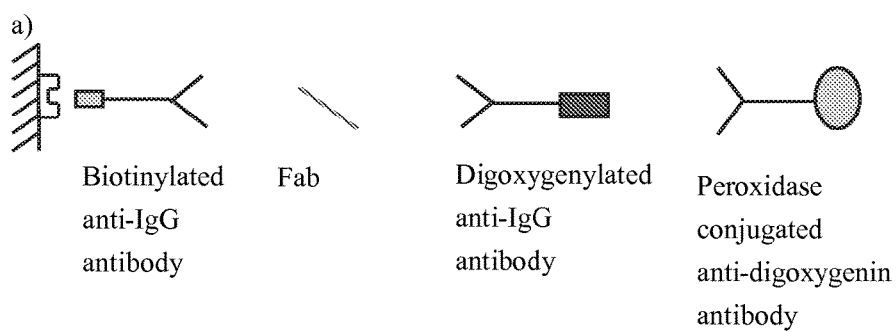
FIGS. 5a) and 5b) Assay for quantifying human antibody derivates in a sample obtained from an experimental animal.
Figure 5:
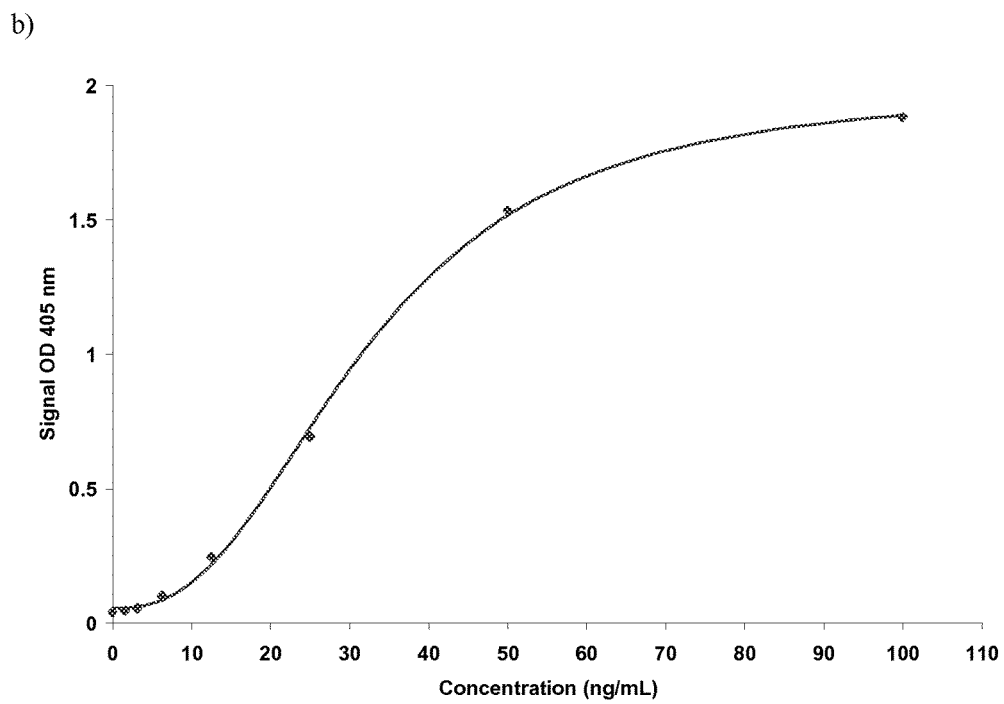
Figure 6:
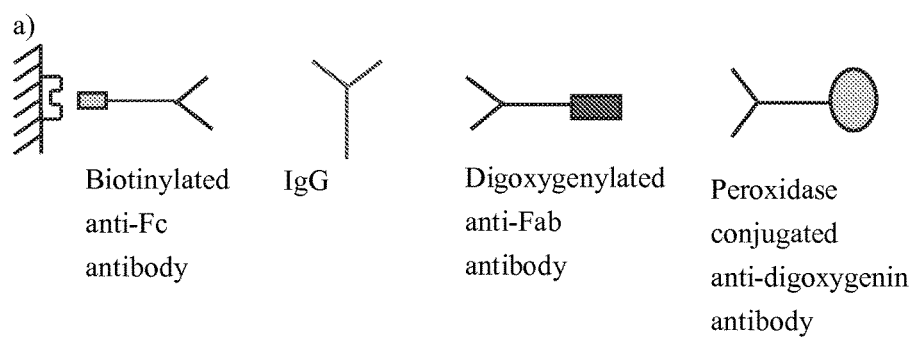
FIGS. 6a) and b) Assay to proof structural integrity of human IgG in an experimental animal.
Figure 6:
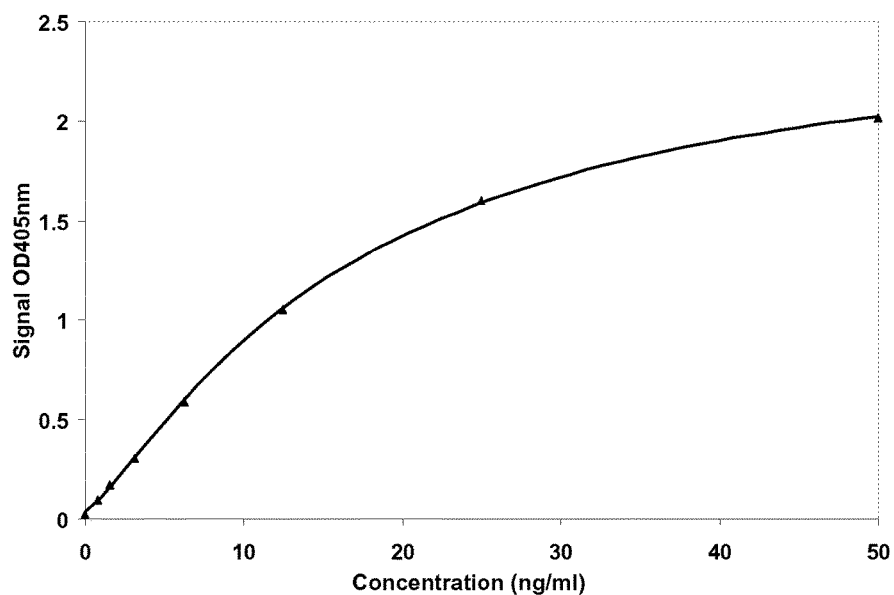

Assay for Quantification of Human Antibody Derivates (e.g. Fab-Fragments) in a Sample from an Experimental Animal Biotinylated antibody M-1.7.10 was bound to streptavidin-coated microtiter plates (SA-MTP) in the first step. The excess of unbound antibody was removed by washing. Samples/standards, e.g. anti-IGFIR antibody Fab fragment, spiked in cynomolgus serum were added to the wells and incubated for 60 min. at ambient temperature, with shaking. After having washed away unbound antibodies, 100 µl digoxigenylated antibody M-1.3.2 was added to each well of the plate. After washing, the bound digoxygenylated antibodies were detected with an anti-digoxygenin antibody-HRP conjugate. Absorbance values of each serum sample were determined in triplicates (see FIG. 5b)).

TABLE 4

| OD data. | | |
| --- | --- | --- |
| ng/ml | OD 405 nm | SD |
| 0.00 | 0.042 | 0.000 |
| 1.56 | 0.047 | 0.000 |

TABLE 4-continued

| | OD data. | |
|---|---|---|
| ng/ml | OD 405 nm | SD |
| 3.13 | 0.057 | 0.002 |
| 6.25 | 0.103 | 0.001 |
| 12.50 | 0.247 | 0.016 |
| 25.00 | 0.694 | 0.007 |
| 50.00 | 1.535 | 0.043 |
| 100.00 | 1.882 | 0.013 |

EXAMPLE 8

Figure 3:
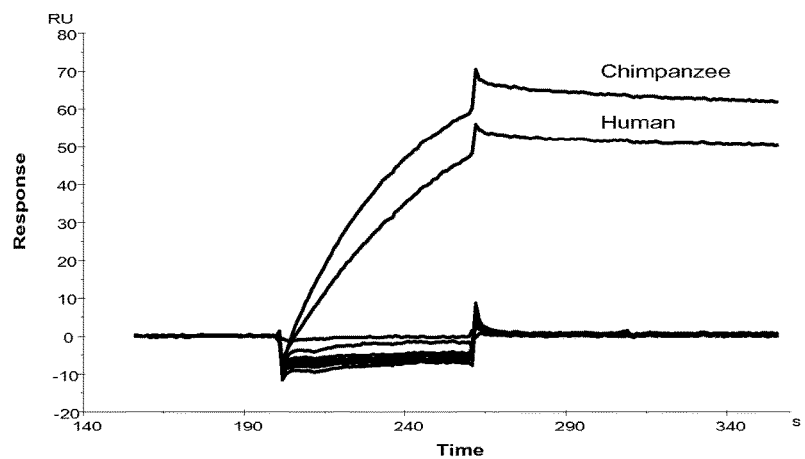
FIGS. 3a)-3c) Exemplary surface plasmon surface resonance diagrams of antibodies.
Figure 3:
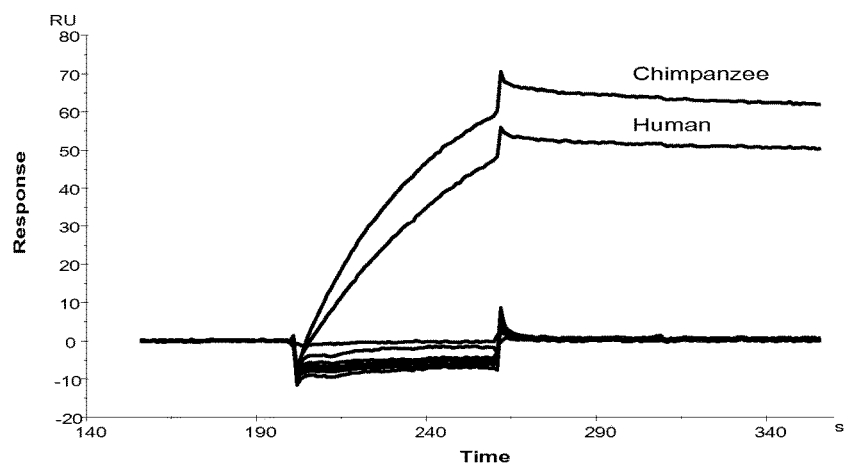
Figure 3:
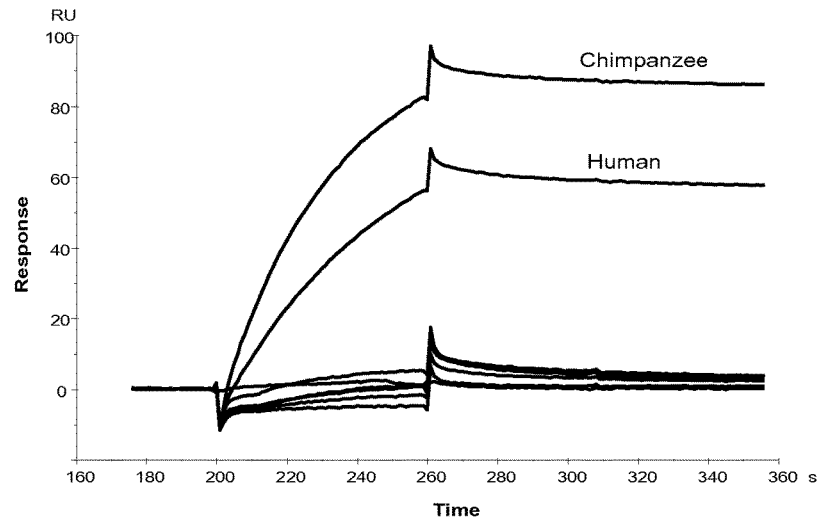
Figure 4:
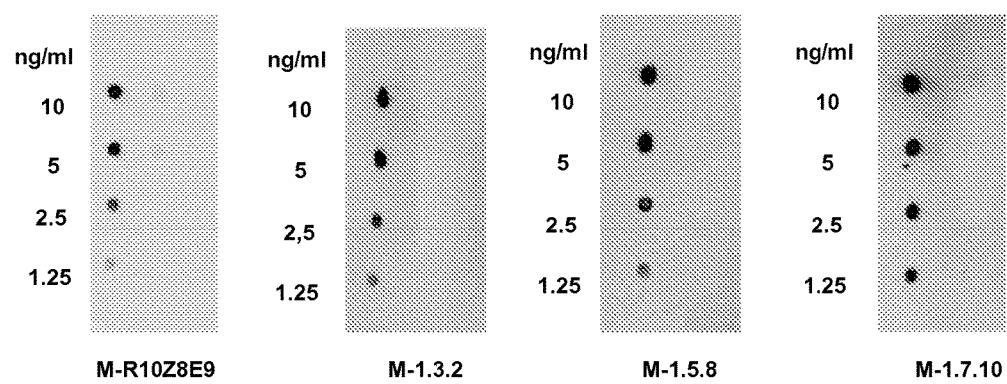
FIG. 4 Dot Blot of anti-human IgG antibodies; as exemplary reference antibody an antibody against P-selectin has been chosen; the reference antibody is dotted is native (left column) and denatured (right column) onto a nitrocellulose membrane and detected by the respective digoxigenylated anti-human IgG antibodies; left to right: M-R10Z8E9, M-1.3.2, M-1.5.8, M-1.7.10.

Assay to Prove Structural Integrity of Human IgG in a Sample from an Experimental Animal Biotinylated antibody M-R10Z8E9 directed against human Fc was bound to streptavidin-coated microtiter plates (SA-MTP) in the first step. The excess of unbound antibody was removed by washing. Samples/standards, e.g. anti-IL13Rα1 antibody, spiked in cynomolgus serum were added to the plate and incubated for 60 min. at ambient temperature, with shaking. After having washed away unbound antibodies, 100 μl digoxygenylated antibody M-1.3.2 was added to the plate. After washing, the bound digoxygenylated antibodies were detected with an anti-digoxygenin antibody-HRP conjugate. Absorbance values of each serum sample were determined in triplicates (see FIG. 3a) for M-1.3.2, FIG. 3b) for M-1.5.8, and FIG. 3c) for M-1.7.10).

TABLE 5

| | OD data. | |
|---|---|---|
| ng/ml | OD 405 nm | SD |
| 0.00 | 0.023 | 0.018 |
| 0.78 | 0.094 | 0.008 |
| 1.56 | 0.172 | 0.007 |
| 3.13 | 0.304 | 0.011 |
| 6.25 | 0.588 | 0.015 |
| 12.50 | 1.051 | 0.007 |
| 25.00 | 1.604 | 0.004 |
| 50.00 | 2.019 | 0.001 |

EXAMPLE 9

Assay for Quantification of Human Antibodies (Human IgG) in a Sample from an Experimental Animal Using a Fc-Fusion Protein (Antigen) in Combination with Anti-Human IgG Antibodies as Reported Herein Soluble extracellular domain of a human receptor X is fused to the Fc-fragment of human IgG1 class. The biotinylated fusion protein (Bi-X-Fc) was bound to streptavidin-coated microtiter plates (SA-MTP) in the first step. The excess of unbound receptor was removed by washing. Afterwards anti-X antibody spiked in cynomolgus serum was bound to the immobilized human receptor X. After washing away unbound substances, the bound anti-X antibody was detected with a) digoxygenylated monoclonal antibody against human Fc fragment (antibody M-R10Z8E9) or with b) digoxygenylated monoclonal antibody against human Fab fragment (antibody M-1.7.10) followed by incubation with a horse-radish peroxidase labeled anti-digoxygenin antibody. Absorbance values of each serum sample are determined in triplicates.

EXAMPLE 10

Dot Blot—Conformation Vs. Linear Epitope

To determine, whether the anti-human IgG antibodies detect a conformation epitope or a linear epitope, a dot-blot analytic was performed.

During this test, the antigen-protein (human IgG) was dotted to a nitrocellulose membrane in a native and a denaturized form. To receive the denaturized form, the antigen-protein was incubated with SDS on a shaker at 37° C. overnight. Both forms were dotted in a concentration series to the membrane. After complete drying of the membrane, the surface was blocked with a blocking buffer (Roti-Block, Roth, Germany) for 60 min. at ambient temperature with shaking. After washing of the membrane, it was incubated with a solution containing digoxygenylated antibody M-R10Z8E9 or one of the three different antibodies M-1.3.2, M-1.5.8, or M-1.7.10. After washing, the bound digoxygenylated antibodies were detected with an anti-digoxygenin antibody-HRP conjugate. The HRP of the antibody-enzyme conjugates catalyzes the color reaction of BM-Blue substrate. The signal can directly be controlled visually and captured with a scanner.

EXAMPLE 11

Assessment of Antibody Binding/Specificity by a Bridging ELISA Assay

To determine which kind of Human IgG subclass is bound by the researched anti human antibodies, a bridging ELISA analytic was performed.

Biotinylated antibodies M-R10Z8E9, M-1.3.2, M-1.5.8 and M-1.7.10 were bound to the streptavidin microtiterplate in the first step. In a second step, human IgG antibodies of different subclasses were incubated. Human IgG1 kappa; human IgG1 lambda; human IgG4; chimeric human IgG1; human IgG2 (polyclonal purified human IgG2) and human IgG3 (polyclonal purified human IgG3) were prepared in a dilution series and incubated to the streptavidin microtiter plate, coated with biotinylated anti human antibody. After a washing step, the same antibodies as used for coating were used as detection antibodies in digoxygenylated form. This means that the same anti human antibody clone was used for coating and detection. For example, one plate was coated with M-1.7.10 Bi and M-1.7.10-Dig was used for detection. After incubation and a washing step, this step was followed by incubation with a horse-radish peroxidase labeled anti-digoxygenin antibody. Absorbance values of each serum sample have been determined in triplicates.

TABLE 6

Resume of bridging ELISA analytics

| | Antibody used for coating/detection | | | |
|---|---|---|---|---|
| Sample | mAb M-R10Z8E9 | mAb M-1.3.2 | mAb M-1.5.8 | mAb M-1.7.10 |
| IgG1-kappa | ++ | ++ | ++ | ++ |
| IgG1-Lambda | ++ | -- | -- | -- |
| IgG4 | ++ | + | + | ++ |
| Chimeric IgG1 | ++ | + | + | ++ |
| IgG2 | + | +- | +- | ++ |
| IgG3 | +- | -- | -- | -- |
| IgG1-kappa Fab | -- | ++ | ++ | ++ |
| IgG1-Lambda Fab | -- | -- | -- | -- |

++ strong binding
+ binding
+- weak binding
-- no binding

The invention claimed is:

1. A hybridoma cell line selected from the group consisting of DSM ACC3006, DSM ACC3007 and DSM ACC3008.

2. An antibody produced by one of the hybridoma cell lines of claim 1.

3. The antibody of claim 2, wherein the hybridoma cell line is DSM ACC3006.

4. The antibody of claim 2, wherein the hybridoma cell line is DSM ACC3007.

5. The antibody of claim 2, wherein the hybridoma cell line is DSM ACC3008.

6. A method for detecting a human or humanized therapeutic antibody comprising a human kappa light chain, or a Fab fragment thereof, in a sample obtained from an experimental animal comprising the steps of
   a) providing a sample to be analyzed, the sample obtained from an experimental animal selected from the group consisting of a canine, a rhesus-monkey, a marmoset, a baboon, and a cynomolgus monkey,
   b) incubating said sample with a capture antibody that is bound to a solid phase, wherein said capture antibody is the antibody of any one of claims 3 to 5,
   c) incubating said sample with a detection antibody that is conjugated to a detectable label so as to form a complex, wherein said detection antibody is the antibody of any one of claims 3 to 5, and
   d) detecting the detectable label on the detection antibody, thereby detecting the therapeutic antibody or Fab fragment thereof.

7. The method of claim 6, wherein the capture antibody is conjugated to biotin and immobilized to the solid phase via avidin or streptavidin.

8. The method of claim 6, wherein the detectable label is digoxigenin and the step of detecting the detectable label is performed via an antibody against digoxigenin.

9. The method of claim 6, further comprising correlating the detectable label that is conjugated to the detection antibody to a concentration of the therapeutic antibody, or Fab fragment thereof, in the sample.

10. The method of claim 6, further comprising washing the sample after incubating the sample with the capture antibody bound to the solid phase.

11. The method of claim 7, wherein the detectable label is digoxigenin and the step of detecting the detectable label is performed via an antibody against digoxigenin.

12. An antibody composition, comprising a mixture of antibodies produced by hybridoma cell line DSM ACC3006, hybridoma cell line DSM ACC3007, and/or hybridoma cell line DSM ACC3008.

* * * * *